United States Patent [19]

Intonti et al.

[11] 4,291,419

[45] Sep. 29, 1981

[54] IMPLANTABLE CARDIAC VALVE PROSTHESIS

[76] Inventors: Francesco Intonti, Località Castelli, 00060 Formello (Prov. Rome); Antonio Intonti, No. 5, Viale Liegi, 00198 Rome, both of Italy

[21] Appl. No.: 121,285

[22] Filed: Feb. 13, 1980

[30] Foreign Application Priority Data

Jun. 13, 1979 [IT] Italy .............................. 49402 A/79

[51] Int. Cl.³ .............................................. A61F 1/22
[52] U.S. Cl. ..................................... 3/1.5; 137/527.8
[58] Field of Search ................... 3/1.5; 137/527, 527.8

[56] References Cited

U.S. PATENT DOCUMENTS 3,476,143  11/1969  Kaster .................................. 3/1.5 X
3,824,629  7/1974  Shiley ..................................... 3/1.5
4,057,857  11/1977  Fettel ..................................... 3/1.5

FOREIGN PATENT DOCUMENTS 1016811  1/1966  United Kingdom ..................... 3/1.5

OTHER PUBLICATIONS

"Mitral Valve Prosthesis" (by Dr. Bruce Paton), The Bulletin of the Dow Corning Center for Aid to Medical Research, vol. 5, No. 4, Oct. 1963, p. 16 (Midland, Mich.).

*Primary Examiner*—Ronald L. Frinks
*Attorney, Agent, or Firm*—Haseltine and Lake

[57] ABSTRACT

A cardiac valve prosthesis comprising an annular metal element into which an occluding element having a truncated cone shape, is half-floatingly mounted, said annular element being provided with means cooperating with said occluding element for defining the maximum aperture of the valve, and abutting elements having very small overall dimensions, arranged in the upstream portion of said annular element, which portion defines the closure position of the occluding element of the prosthesis.

2 Claims, 7 Drawing Figures

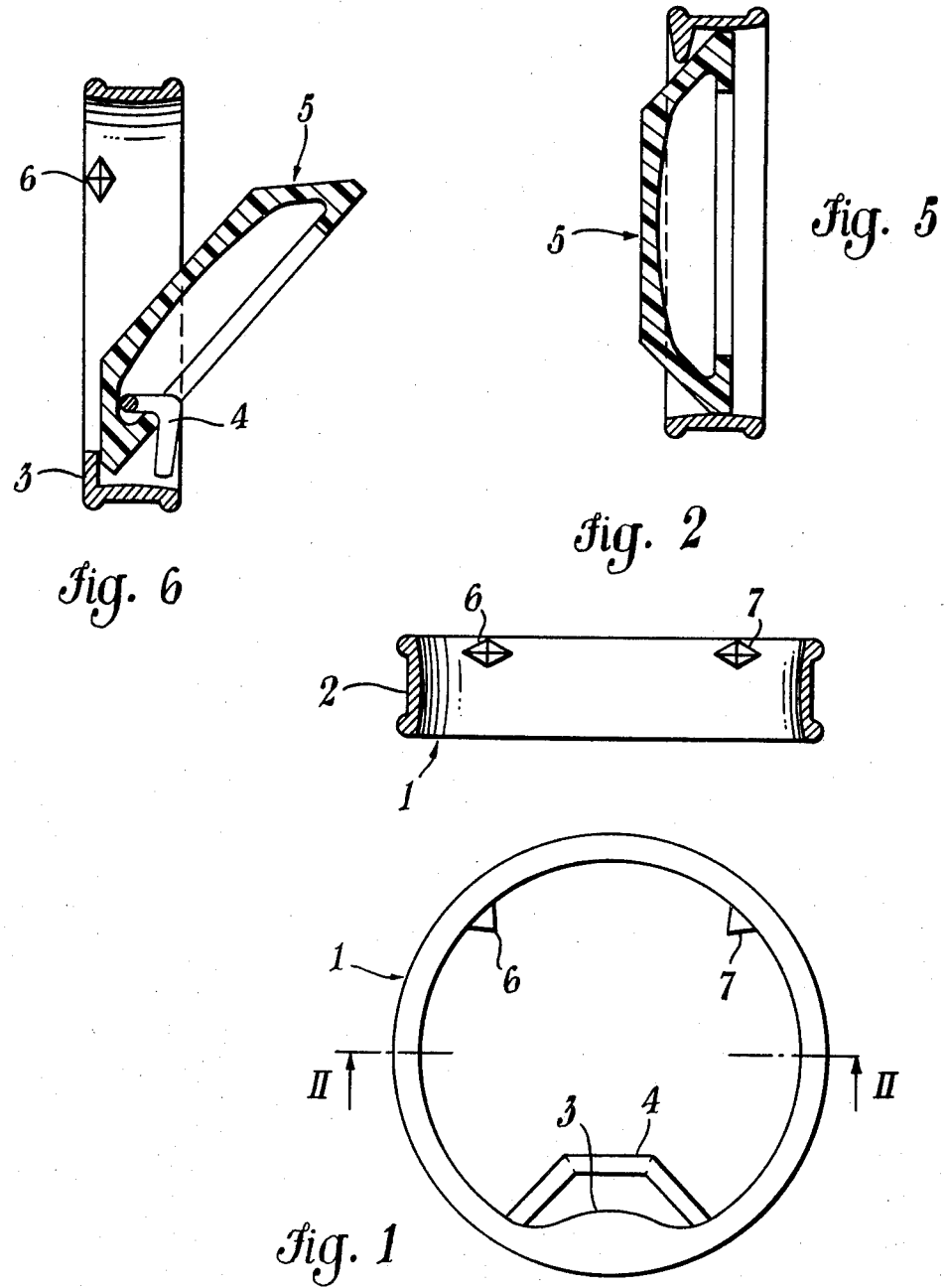

IMPLANTABLE CARDIAC VALVE PROSTHESIS

The present invention relates to cardiac valve prostheses intended to be placed in a mitralic, aortic or tricuspid position or in valve tubes for pulmonary implantations.

Cardiac valve prostheses are already well known. Among several solutions of problems connected with the occluding element, there are two prosthesis kinds, namely the Bjork—Shiley prosthesis and Lillehei—Kaster prothesis which utilize an eccentric occluding element. However, these known prostheses (BS), (LK) with the eccentric occluding element give rise to several disadvantages owing to that the structural elements of the prosthesis hinder a free blood flux and, moreover, the abutting rims of the occluding elements cause at the closure stage a traumatizing effect on the red globules.

An object of the present invention is that to provide a cardiac valve prosthesis of the kind including an eccentric occluding element, improved with respect to the known ones, which allows to attain a bloody flux substantially free of vortex when the valve is open and an optimal closure effect with a minimum traumatizing effect on the red globules.

According to the present invention it is provided a cardiac valve prosthesis comprising an annular metal element, having a truncated cone shape, mechanical stop elements for defining a maximum opening of the valve and abutting elements, having a small overall dimensions, which define the closure position of the occluding element of the prosthesis.

The present invention will be now disclosed with reference to a preferred embodiment thereof as shown only for illustrative and not limitative purpose in the figures of the enclosed drawings, in which:

FIG. 1 shows a plan view of the annular element of the valve prosthesis according to the present invention;

FIG. 2 shows a section view along the line II—II of FIG. 1;

FIG. 5 shows a section view along the line V—V of FIG. 3;

FIG. 6 shows a view similar to that of FIG. 4, but with the occluding element in its open position;

Figure 3:
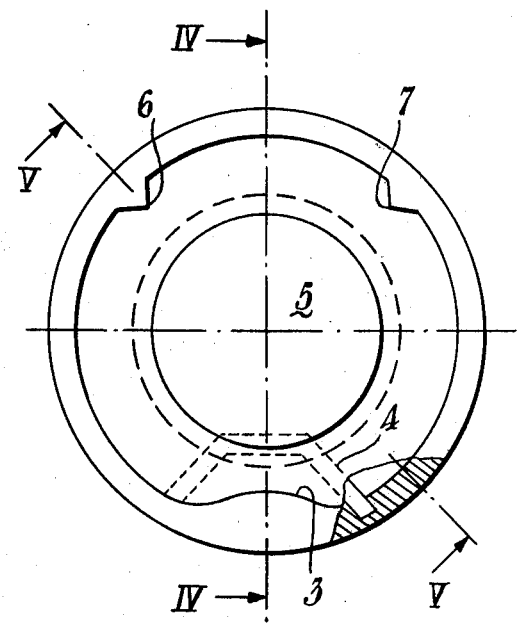
FIG. 3 shows a view similar to that of FIG. 1, with the occluding disc in its closed position.

Referring now to the drawings, the prosthesis according to the invention comprises an annular metal element 1 adapted to receive in an outer peripheral recess 2, a collar of synthetic tissue, not shown in the drawings, apt to be sutured in situ during the surgical valve implantation.

In its inner portion the annular element comprises a radiused projection 3 cooperating with a filiform metal bracket 4, preferably having a circular cross-section, which by cooperating with the occluding element, indicated with the reference numeral 5, forms the articulation of the valve.

The annular element has, moreover, in its inner portion two stops 6,7 provided for determining the true closure position of the occluding element 5.

The stops 6,7 are, preferably, shaped as double triangular section stops so as to form two pyramidal projection with a relatively low profile and limited occlusion of the open port of the valve and, furthermore, said stops form a small abutting surface for the stop wall of the occluding element 5 to reduce at the utmost degree the hemolyze.

The occluding element indicated in its assembly with 5, preferably has a truncated-cone shaped outer surface and a circular symmetry and is provided with a portion 8 folded towards the interior thereof, which portion cooperates with both the bracket 4 and projection 3 to form the articulation of the valve element.

Figure 4:
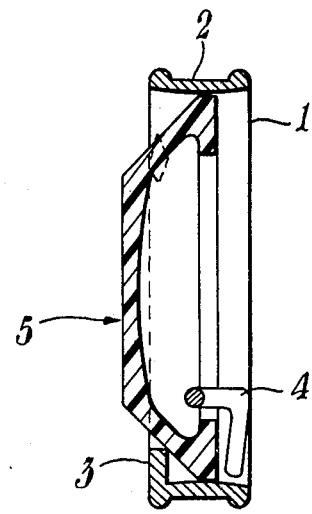
FIG. 4 shows a section view along the line IV—IV of FIG. 3.
Figure 7:
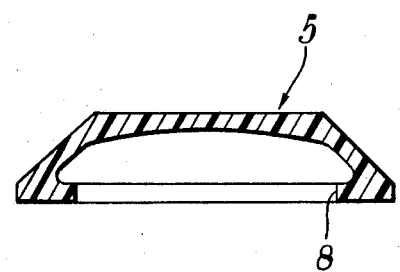
FIG. 7 shows a view in diametral section of the occluding element of the prosthesis according to the invention.

The operation of the valve prosthesis according to the invention clearly results from the FIGS. 4, 5, 6 which show the end position of aperture and closure.

It should be noted that the single parts of the prosthesis are sized in such a manner that the occluding element 5 is floating and thus free to rotate during the operation, continuously changing the stop points both at the aperture and closure so as to uniformly distribute the wear onto all the mechanical abutting parts.

The occluding element 5 may be provided with a x-ray opaque reference member for the dynamical visualization thereof during the radioscopic observations.

The materials are the same as usually employed for implantable prostheses of this kind.

The occluding element preferably consists of carbon pyrolyzate on graphite nucleus of "Delrin" or other similar synthetic materials well known for these purposes.

It should be noted that besides the feature of low blood traumatization, the prosthesis according to the invention provides extremely short occlusion times since the angular excursion of the occluding element is selected within the 45° angle, which angle is very small with respect to the other known constructions with an excursion angle of the occluding element ranging from 60° to 80°.

Moreover it is also to be noted that the hollow conformation of the occluding element as defined by the folded portion 8, facilitates the capture of the sphygmic wave and thus the closure of the valve itself.

The present invention has been disclosed with reference to a preferred embodiment thereof, but it will be understood that several modifications and changes might be entered without thereby departing from the scope of the invention.

We claim:

1. An implantable cardiac valve prosthesis, comprising:
   (a) an annular element;
   (b) a hollow occluder having a truncated cone shape and an articulated joint means for connecting said occluder to said annular element in which said articulated joint means comprises a filiform bracket secured at both ends to an inner wall of said annular element and to a radiused protuberance projecting from said inner wall in parallel to said bracket, said occluder further comprising a folded portion toward its interior into which folded portion said filiform bracket is inserted, said protuberance determining an aperture angle of said occluder which is 45° or less; and
   (c) two stop elements provided on said inner wall symmetrically opposite to said protuberance.

2. The implantable cardiac valve prosthesis as recited to claim 1 in which said stop elements comprise pyramidal punctiform abutments against which said occluder abuts in closed position, whereby, the abutment surfaces of the occluder and, thus, the emolyse are substantially reduced.

* * * * *